US006824796B2

(12) United States Patent
Pusateri et al.

(10) Patent No.: US 6,824,796 B2
(45) Date of Patent: Nov. 30, 2004

(54) EXTRACTION OF NON-POLAR ISOTHIOCYANATES FROM PLANTS

(75) Inventors: Donald J. Pusateri, Hemet, CA (US); Tamara R. Kizer, Menifee, CA (US); Alex N. Lowry, Riverside, CA (US)

(73) Assignee: Access Business Group International LLC, ADA, MI (US)

( * ) Notice: Subject to any disclaimer, the term of this patent is extended or adjusted under 35 U.S.C. 154(b) by 68 days.

(21) Appl. No.: 10/176,869

(22) Filed: Jun. 21, 2002

(65) Prior Publication Data

US 2003/0235634 A1 Dec. 25, 2003

(51) Int. Cl.$^7$ .............................................. A61K 35/78
(52) U.S. Cl. ...................................... 424/755; 424/725
(58) Field of Search ................................... 424/725, 755

(56) References Cited

U.S. PATENT DOCUMENTS

| | | |
|---|---|---|
| 2,987,399 A | 6/1961 | Goering |
| 3,044,876 A | 7/1962 | Goering |
| 3,615,648 A | 10/1971 | Barros |
| 4,713,467 A | 12/1987 | Telschow et al. |
| 4,997,967 A | 3/1991 | Hässig |
| 5,231,209 A | 7/1993 | Chung et al. |
| 5,411,986 A | 5/1995 | Cho et al. |
| 5,686,108 A | 11/1997 | Pusateri et al. |
| 5,882,646 A | 3/1999 | Pusateri et al. |

OTHER PUBLICATIONS

*Phenolic Compounds in Virgin Olive Oils: Fractionation by Solid Phase Extraction and Anitoxidant Activity Assessment,* Author(s): Litridou et al., J. Sci. Food Agric., 1997, 74, pp. 169–174.

*Evolution of Phenolic Compounds in Virgin Olive Oil During Storage,* Author(s): Cinquanta et al., JAOCS, vol. 74, No. 10 (1997), pp. 1259–1264.

*Antioxidant Activity of Tocopherols and Phenolic Compounds of Virgin Olive Oil,* Author(s): M. Baldioli et al., JAOCS, vol. 73, No. 11 (1996), pp. 1589–1593.

*Primary Examiner*—Christopher R. Tate
(74) *Attorney, Agent, or Firm*—Brinks Hofer Gilson & Lione; G. Peter Nichols

(57) ABSTRACT

A method of extracting non-polar isothiocyanates from a plant includes providing fresh or dehydrated plant material that contains at least one glucosinolate that will form a corresponding non-polar isothiocyanate, and endogenous myrosinase enzyme. Water is added to the plant material and milled, and oil is added thereafter to the water and plant mixture. This mixture is then homogenized after which the oil phase is separated from water phase and solids, such that the non-polar isothiocyanate(s) partition into the oil phase. A stable composition made according to the method includes at least one non-polar isothiocyanate and a vegetable oil. A dietary supplement may be formulated from the stable composition.

13 Claims, 1 Drawing Sheet

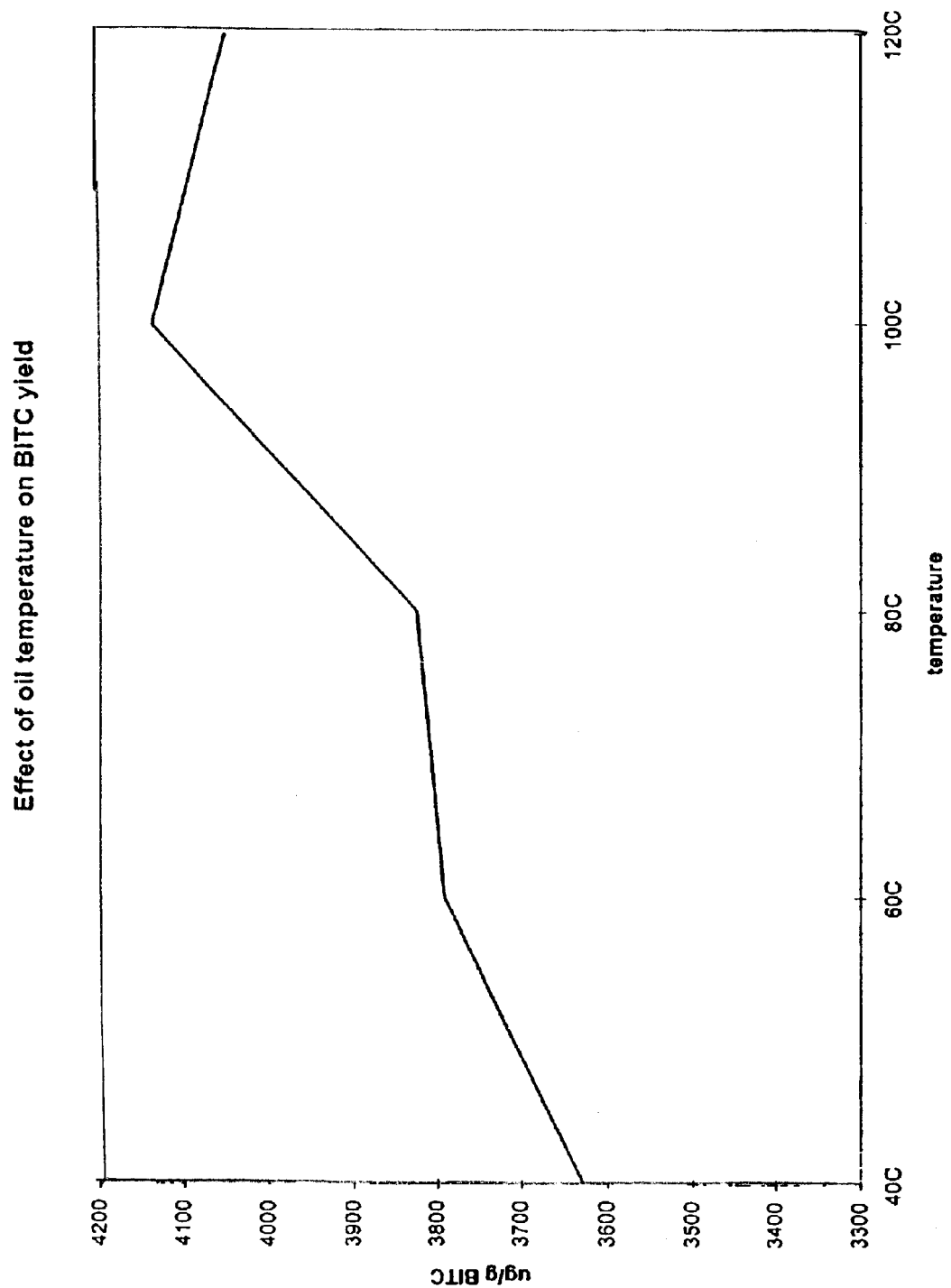

EXTRACTION OF NON-POLAR ISOTHIOCYANATES FROM PLANTS

BACKGROUND

The present invention relates to the extraction of non-polar isothiocyanates from plants and stable compositions of the same for use as dietary supplements.

Finding effective methods for preventing cancer has been a major research goal of the past century. A great deal of research has been done on the impact diet has on a person's risk of cancer. Numerous studies show that eating vegetables, especially vegetables belonging to the family Brassicaceae, such as *brassica* vegetables, may reduce the risk of developing cancer of various organs. See, for example, U.S. Pat. No. Re. 36,784, which is hereby incorporated by reference.

These *brassica* vegetables are believed to reduce the risk of cancer because they contain glucosinolates that are converted into isothiocyanates by contact with endogenous myrosinase enzymes when the cells of the vegetables are disrupted. Some isothiocyanates are potent phase II enzyme inducers, which can protect cells against the toxic and neoplastic effects of carcinogens. Therefore, a number of isothiocyanates from the brassica vegetables are biologically useful in preventing cancer.

The *brassica* vegetables may contain glucosinolates that are converted to isothiocyanates that are characterized as being either polar or non-polar. Certain non-polar isothiocyanates are desirable because of their implication in the prevention of certain cancers, most notably lung cancer. Benzyl isothiocyanate (BITC) and phenethyl isothiocyanate (PEITC) are particularly useful in the prevention of lung cancer.

Although it is desirable to include non-polar isothiocyanates in dietary supplements, it is difficult to do so using the present methods. Extraction of isothiocyanates from vegetables tends to be carried out using an aqueous solvent, which is more effective for extracting polar isothiocyanates than non-polar isothiocyanates. Furthermore, some of the biologically important non-polar isothiocyanates tend to be volatile and unstable once extracted. Thus, a stable composition suitable for use in dietary supplements is not available according to currently used procedures.

A method for extracting non-polar isothiocyanates from plant materials, especially those that are important to health and disease prevention, is needed. There is also a need to provide stable compositions containing non-polar isothiocyanates that can be conveniently delivered to consumers wanting them.

SUMMARY

The methods of the present invention solve the problems associated with prior art extraction methods to produce compositions of non-polar isothiocyanates. These compositions stabilize the isothiocyanates and are useful for dietary supplements.

In one aspect of the invention, a method of extracting a non-polar isothiocyanate from a plant includes providing fresh or dehydrated plant material having at least one glucosinolate that will form a corresponding non-polar isothiocyanate and having at least one endogenous myrosinase enzyme. Thereafter, water is added to the plant material and the mixture is homogenized, to allow for conversion of the glucosinolate(s) to isothiocyanate(s). A vegetable oil is then added to the water and plant material homogenate and the resulting mixture is blended. Finally, the oil phase is separated from the aqueous phase and solids such that the non-polar isothiocyanates partition into the oil phase.

In another aspect of the invention, a stable composition comprises a non-polar isothiocyanate and a vegetable oil.

In still another aspect of the invention, a method of preventing cancer comprises administering the stable composition.

In still another aspect of the invention, a dietary supplement comprises a non-polar isothiocyanate present in a therapeutically effective amount to help with cancer prevention, a vegetable oil-based carrier and from about 0.1% to about 0.5% of mixed tocopherols or one of its individual constituents, such as alpha-tocopherol.

The above and other aspects and advantages of the present invention will become apparent from the following detailed description of the preferred embodiments. It is noted that, unless otherwise stated, all percentages given in this specification and the appended claims refer to percentages by weight.

BRIEF DESCRIPTION OF THE DRAWING

FIG. 1 is a graph of the effect of oil temperature on the yield of BITC.

DETAILED DESCRIPTION

As described above, the plant material contains at least one glucosinolate that will form a corresponding non-polar isothiocyanate and at least one endogenous myrosinase enzyme. The plant material may be either fresh or dehydrated. The plant material may be any plant having the desired characteristics.

Generally, the plant material is from the family Brassicaceae, the mustard family, of which glucosinolates are characteristic constituents. Most preferably, the plant material includes, but is not limited to, watercress (*Nasturtium officinale*), garden cress (*Lepidium sativum*), nasturtium (*Tropaeolum majus*), wasabi (*Wasabi japonica*), and horseradish (*Amoracia rusticana*).

The plant material may be a single species or a combination of species. Watercress is an especially good source of PEITC, and garden cress is an especially good source of BITC.

When harvesting the plant material from which the isothiocyanates are to be extracted, care should be taken to avoid damaging or disrupting the cell walls of the plant material. This type of damage can occur through crushing, shredding, or macerating the fresh plant material. Disruption of the cell walls should be avoided because it can cause premature conversion of the glucosinolates to the desired non-polar isothiocyanates by the action of the endogenous myrosinase enzyme. Often, the non-polar isothiocyanates are not very stable, as noted above. Thus, non-polar isothiocyanates formed during the harvesting of the plant material may decompose before they are extracted, resulting in a reduced yield.

Preferably, the plant material is processed immediately after harvest to maximize the amount of isothiocyanates in the extract. Alternatively, the plant material should be dehydrated shortly after it is harvested. Dehydrating the plant material can fix its phytochemical content if it is to be stored or transported prior to extraction or otherwise cannot be immediately processed.

After harvesting, the plant material can be whole or coarsely chopped before it is dehydrated; however, some premature conversion of glucosinolates to isothiocyanates will occur if they are chopped. Dehydration can be accomplished by any method that does not destroy the parent glucosinolate or the endogenous myrosinase enzyme. For example, dehydration may be carried out by forced draft methods using a forced draft oven.

The dehydration period is in a range of about 3 to about 36 hours, and preferably about 24 hours. In one embodiment, the plant material is dehydrated in an oven at a temperature ranging from about 40° C. to about 120° C., and preferably from about 40° C. to about 100° C., and more preferably from about 40° C. to about 60° C. The endogenous myrosinase enzymes survive the dehydration process when temperatures from about 40° C. to about 60° C. are used. As a result, the need to add exogenous myrosinase enzyme in the extraction step to effect conversion of the glucosinolate to the isothiocyanate is reduced.

Extracting Isothiocyanates

A preferred method of extracting non-polar isothiocyanates involves providing fresh or dehydrated plant material, adding water, and homogenizing the mixture to form a plant material and water homogenate. A vegetable oil is then added to the homogenate and the resulting mixture is blended. The blending can be carried out in any suitable apparatus. As a result of the blending, the non-polar isothiocyanates are extracted into the oil phase.

If dehydrated plant material is used, it should be milled into a powder first to increase its surface area and then hydrated with water prior to the extraction of the isothiocyanates into the vegetable oil. The milling and hydration steps allow the conversion of the glucosinolates to isothiocyanates by the action of the endogenous or added exogenous myrosinase enzyme. Next, the water and plant mixture is homogenized, and then the oil is added and the mixture blended.

The water is preferably de-ionized water. Preferably, the vegetable oil is selected from the group consisting of safflower oil, corn oil, olive oil, walnut oil, sesame oil, hazelnut oil, canola oil, grape seed oil, rice oil, avocado oil and mixtures thereof. It is contemplated that other oils may be used, so long as they do not interfere with the efficacy of the isothiocyanates and humans can safely ingest them.

To further protect the non-polar isothiocyanates from decomposing, the vegetable oil is optionally treated with an oil soluble antioxidant. Nearly any antioxidant, such as tocopherols and carotenoids, can be used so long as it protects and does not interfere with the function of the non-polar isothiocyanate. Preferably, the antioxidant is mixed tocopherols or one of its individual constituents, such as alpha-tocopherol. Preferably, the antioxidant is present in the oil in an amount ranging from about 0.1% to about 0.5% by weight. More preferably, the amount of antioxidant in the oil ranges from about 0.2% to about 0.4% by weight.

The mixture of water, fresh or dehydrated plant material and oil is then blended by any method known in the art, preferably high-shear blending. Blending can be carried out using an industrial blender, liquiverter, colloid mill, or other methods.

The water acts as a solvent for the polar glucosinolates and helps to liberate these compounds from the plant matrix upon cell disruption. The water also activates the endogenous myrosinase enzyme in the dry plant material, and acts as the medium to facilitate the glucosinolate hydrolysis and formation of the corresponding isothiocyanate. Optionally, an exogenous myrosinase enzyme source may be added to the mixture to aid the conversion process.

A certain period of time of contact of the water with the plant material may be needed for the conversion of the glucosinolates to the isothiocyanates. When fresh plant material is used, the conversion to isothiocyanates may be almost instantaneous; however, for dehydrated plant materials, a contact time of up to four hours may be necessary for the conversion. Upon formation of the isothiocyanates, the oil may be added. Once the oil is added and the mixture homogenized, the phases may be immediately separated. Preferably, a period of contact time with the oil of at least one hour is provided to allow the extraction to take place, and more preferably the period of time is at least about 4 hours.

After the vegetable oil is added and blended, the polar isothiocyanates remain in the water phase, and the non-polar isothiocyanates, such as PEITC and BITC, partition into the oil phase. To speed the extraction and maximize the amount of non-polar isothiocyanates recovered from the mixture, the oil is optionally heated. The oil temperature during extraction may be in a range of about 40° C. to about 140° C., preferably from about 60° C. to about 120° C. The oil extraction should be given sufficient time to complete, preferably at least about four hours.

The oil and water phases can then be separated by any method known in the art. Methods of separation include liquid-liquid centrifugation or a settling-and-decanting process.

The oil phase separated as described above contains at least one non-polar isothiocyanate. The oil protects non-polar isothiocyanates from decomposition or volatilization and thus provides a stable composition containing non-polar isothiocyanates. When antioxidants have been added to the oil, additional stabilization of the non-polar isothiocyanates is provided. The stable composition is suitable for administration to prevent cancers, in particular lung cancer.

Dietary Supplement

The present invention also contemplates a dietary supplement that contains a stable composition comprising at least one non-polar isothiocyanate and an oil prepared by the method described above. The dietary supplement may optionally contain other additives such as polar isothiocyanates and other nutrients shown to play an important role in health and disease. The dietary supplement can be delivered in any pharmaceutically acceptable vehicle. Preferably the vehicle is a soft gel cap, tablet, or two-piece hard cap. Gel caps are particularly preferred because they are especially amenable to the oil matrix composition containing the non-polar isothiocyanates and provide a good oxygen barrier. Alternatively, the oil extract may be emulsified with excipients and water and dried into a powder for other delivery systems, such as, but not limited to, two-piece hard caps or tablets.

The dietary supplement should contain enough of the non-polar isothiocyanates to be therapeutically effective in preventing cancers, especially lung cancer, when taken as directed. It is estimated that the effective amount of the PEITC and/or BITC would be in a range of about 1–5 mg/day.

Optionally, the dietary supplement can contain other ingredients, including pharmaceutically acceptable carriers, vitamins, minerals, other phytochemicals, buffers, and other additives.

EXAMPLES

The following examples are merely intended to illustrate the method of the present invention, and are not intended to be limiting.

Example 1

To determine the effect of dehydration temperatures and the addition of exogenous myrosinase enzyme on the yield of non-polar isothiocyanates, the following experiment was conducted. Five samples of watercress plants were dehydrated at 50° C., 60° C., 70° C., 80° C., and 100° C., respectively, for 24 hours in a forced draft oven. All samples were run with and without the addition of exogenous myrosinase (thioglucosidase, EC 3.2.3.1) enzyme.

200 mg of each of the dehydrated plants were added to a 50 mL conical vial with 10 mL water and homogenized for 2 minutes. One set of samples contained 15 mg thioglucosidase enzyme and one contained no added thioglucosidase enzyme. Samples were extracted by adding 25 mL methylene chloride, homogenizing for one minute, followed by centrifugation for two minutes at 4,000×g. The methylene chloride layer was collected and filtered through a glass microfiber filter and dried over sodium sulfate. The extraction was repeated a second time, the methylene chloride fractions pooled, and the filter was washed with approximately 40 mL of fresh methylene chloride. Samples were concentrated to 500 microliters in vacuo and brought up to 2 mL with methylene chloride for GC analysis.

The samples were evaluated for PEITC content. The samples where exogenous thioglucosidase enzyme was added had a higher PEITC content than the samples where the enzyme was not added. Also, the samples that were dehydrated at 50° C. had a higher PEITC content than the samples that were dehydrated at higher temperatures.

Example 2

Both PEITC and BITC are not soluble in water. Gel cap delivery systems incorporating carotenoids and tocopherols in oil matrices have been successful in as far as protection from volatilization and oxidation. Garden cress powder, prepared by drying at 45° C. and containing about 2500 mg/g BITC, and watercress powder, prepared by drying at 50° C. and containing about 4000 mg/g PEITC, were mixed in equal parts. From the mixture, 500 mg were added to a 50 mL conical vial to which 10 mL of water was added and the mixture homogenized for 2 minutes. The mixture was extracted twice with 10 mL safflower oil using homogenization at level 6 (Omni 5000 Mixer) for one minute and centrifuged for 3 minutes at 8,000×g. The oil fractions were collected, pooled and the volume brought up to 25 mL. This experiment showed that an oil extract from watercress and garden cress could be readily prepared for incorporation into a gel cap, which is suitable as a dietary supplement.

Example 3

Various oils were tested in the extraction of BITC from garden cress powder. The powder was prepared by dehydration at 70° C. for 24 hours and then milling. The extractions were carried out by placing 200 mg of the garden cress powder in a 50 mL conical vial, adding 10 mL water and homogenizing for 2 minutes. 10 mL of oil was added and the mixture homogenized for 1 minute followed by centrifugation for 2 minutes to separate the mixture into phases. In some experiments, a second extraction with 10 mL of oil was carried out. The oil phases were collected and tested for BITC. The BITC concentrations were measured by G.C. The resulting concentrations of BITC are indicated below:

| Oil | µg/g BITC |
| --- | --- |
| Corn oil | 4682 |
| Rice oil | 4315 |
| Canola oil | 6237 |
| Olive oil | 5203 |
| Soy oil | 4918 |
| Safflower oil | 4111 |
| Grape seed oil | 5761* |
| Walnut oil | 7580* |

*These extractions used 1 × 10 mL oil; the others were 2 × 10 mL oil.

This experiment showed that a variety of oils are suitable for extracting the non-polar isothiocyanates.

Example 4

The temperature (T) of the oil during extraction was varied. Experiments were carried out on garden cress powder as described above. The results are shown below.

| T (° C.) | µg/g BITC |
| --- | --- |
| 40 | 3628 |
| 60 | 3792 |
| 80 | 3826 |
| 100 | 4138 |
| 120 | 4051 |

As the temperature increased, the concentration of BITC in the oil increased. FIG. 1 shows that the optimal extraction occurs at about 100° C. and begins to decline at about 120° C. Thus, heating the oil at a temperature ranging from 40–120° C. improves the uptake of non-polar isothiocyanates by the oil.

Example 5

The extraction of BITC from garden cress using a typical organic solvent, methylene chloride ($CH_2Cl_2$) and oil were compared to test efficiency of the oil. Larger volumes of BITC could be extracted into vegetable oil, vs. $CH_2Cl_2$.

| Sample | µg/g BITC |
| --- | --- |
| 1 using $CH_2Cl_2$ | 2297 |
| 2 using $CH_2Cl_2$ | 1621 |
| 3 using enzyme and $CH_2Cl_2$ | 2508 |
| Average oil extraction from Example 3 | 5351 |

Example 6

The amount of time between addition of water to the garden cress powder followed by a 1 min. centrifuge and extraction with $CH_2Cl_2$ was tested and the results are shown below:

| Sample and time (t) | µg/g BITC |
| --- | --- |
| 1 t = 0 | 2297 |
| 2 t = 0 | 1621 |

| Sample and time (t) | μg/g BITC |
|---|---|
| 3 t = 4 hr | 7653 |
| 4 t = 4 hr | 7180 |

This experiment indicates the amount of time required for BITC formation after dehydrated plant material is hydrated, without the addition of an exogenous source of myrosinase.

Example 7

BITC and PEITC were purchased from Aldrich (Sigma-Aldrich, Milwaukee, Wis.) and dissolved in safflower oil to determine how much of the non-polar isothiocyanates could be stored in the oil. Over 100 mg of each BITC and PEITC were successfully dissolved in 1 ml of safflower oil to give the following composition, containing greater than 100,000 ppm of each of the non-polar isothiocyanates:

| Ingredient | % Volume | ppm (mg/L) |
|---|---|---|
| PEITC | 9.59 | 104,540 |
| BITC | 11.50 | 129,430 |
| Safflower oil | 78.91 | |

This demonstrates that the oil matrix can hold large concentrations of non-polar isothiocyanates and will therefore be useful as a carrier for PEITC and BITC.

Of course, it should be understood that a wide range of changes and modifications can be made to the embodiments described above. It is intended that the foregoing description illustrates rather than limits this invention, and that it is the following claims, including all equivalents that define this invention.

What is claimed is:

1. A method of extracting a non-polar isothiocyanate from a plant, comprising:
   a. providing at least one plant material that contains at least one glucosinolate and a myrosinase enzyme, wherein the at least one glucosinolate will form a corresponding non-polar isothiocyanate;
   b. adding water to the plant material;
   c. homogenizing the plant material and water to form a plant material and water homogenate;
   d. adding a vegetable oil to the plant material and water homogenate to form a mixture;
   e. blending the mixture; and
   f. separating an oil phase and a water phase such that at least one non-polar isothiocyanate partitions into the oil phase.

2. The method of claim 1 wherein step (b) further comprises adding an exogenous myrosinase enzyme.

3. The method of claim 1 further comprising heating the oil.

4. The method of claim 3 wherein the heating is at a temperature in a range of about 40° C. to about 120° C.

5. The method of claim 1 wherein the plant material is fresh.

6. The method of claim 1 wherein step (a) further comprises dehydrating the plant material.

7. The method of claim 6 wherein the plant material, water, and vegetable oil have a ratio of about 1:50:30, respectively.

8. The method of claim 1 wherein the plant material comprises a *brassica* plant.

9. The method of claim 8 wherein the plant is selected from the group consisting of watercress, garden cress, nasturtium, wasabi, horseradish, and mixtures thereof.

10. The method of claim 1 wherein the vegetable oil is selected from the group consisting of safflower oil, corn oil, olive oil, walnut oil, sesame oil, hazelnut oil, canola oil, grapeseed oil, rice oil, avocado oil, and mixtures thereof.

11. The method of claim 1 further comprising fortifying the vegetable oil with an oil soluble antioxidant.

12. The method of claim 11 wherein the antioxidant is selected from the group consisting of mixed tocopherols and an individual constituent of the mixed tocopherols.

13. A method of extracting a non-polar isothiocyanate from a plant, comprising:
   a. providing at least one plant material that contains at least one glucosinolate and a myrosinase enzyme, wherein the at least one glucosinolate will form corresponding non-polar isothiocyanate;
   b. adding water to the plant material;
   c. homogenizing the plant material and water to form a plant material and water homogenate;
   d. adding a vegetable oil to the plant material and water homogenate to form a mixture; and,
   e. separating an oil phase and a water phase such that at least one non-polar isothiocyanate partitions into the oil phase.

* * * * *